United States Patent
Anderheggen et al.

(10) Patent No.: US 11,033,483 B2
(45) Date of Patent: *Jun. 15, 2021

(54) PASTE-LIKE BLEACHING AGENT AND METHOD FOR GENTLE OXIDATIVE HAIR LIGHTENING

(71) Applicant: Henkel AG & Co. KGaA, Duesseldorf (DE)

(72) Inventors: Bernd Anderheggen, Moenchengladbach (DE); Burkhard Mueller, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 703 days.

This patent is subject to a terminal disclaimer.

(21) Appl. No.: 15/610,272

(22) Filed: May 31, 2017

(65) Prior Publication Data

US 2017/0340553 A1  Nov. 30, 2017

Related U.S. Application Data

(60) Provisional application No. 62/345,105, filed on Jun. 3, 2016.

(30) Foreign Application Priority Data

May 31, 2016  (DE) .......................... 102016209464.5

(51) Int. Cl.

| | | |
|---|---|---|
| *A61Q 5/08* | (2006.01) | |
| *A61K 8/92* | (2006.01) | |
| *A61K 8/362* | (2006.01) | |
| *A61K 8/44* | (2006.01) | |
| *A61K 8/43* | (2006.01) | |
| *A61Q 5/10* | (2006.01) | |
| *A61K 8/22* | (2006.01) | |
| *A61K 8/365* | (2006.01) | |
| *A61K 8/49* | (2006.01) | |
| *A61K 8/36* | (2006.01) | |
| *A61K 8/02* | (2006.01) | |
| *A61K 8/23* | (2006.01) | |
| *A61K 8/25* | (2006.01) | |
| *A61K 8/31* | (2006.01) | |
| *A61K 8/34* | (2006.01) | |
| *A61K 8/46* | (2006.01) | |
| *A61K 8/73* | (2006.01) | |
| *A61K 8/81* | (2006.01) | |
| *A61K 8/86* | (2006.01) | |

(52) U.S. Cl.
CPC ............ *A61K 8/922* (2013.01); *A61K 8/0216* (2013.01); *A61K 8/22* (2013.01); *A61K 8/23* (2013.01); *A61K 8/25* (2013.01); *A61K 8/31* (2013.01); *A61K 8/342* (2013.01); *A61K 8/36* (2013.01); *A61K 8/362* (2013.01); *A61K 8/365* (2013.01); *A61K 8/43* (2013.01); *A61K 8/44* (2013.01); *A61K 8/463* (2013.01); *A61K 8/4946* (2013.01); *A61K 8/73* (2013.01); *A61K 8/731* (2013.01); *A61K 8/8117* (2013.01); *A61K 8/86* (2013.01); *A61K 8/92* (2013.01); *A61Q 5/08* (2013.01); *A61Q 5/10* (2013.01); *A61K 2800/31* (2013.01); *A61K 2800/48* (2013.01); *A61K 2800/882* (2013.01)

(58) Field of Classification Search
None
See application file for complete search history.

(56) References Cited

U.S. PATENT DOCUMENTS

| | | | | |
|---|---|---|---|---|
| 2006/0269492 | A1* | 11/2006 | Narasimhan | ............ A61K 8/23 424/62 |
| 2011/0038818 | A1* | 2/2011 | Onyebuagu | ............ A61K 8/042 424/62 |
| 2011/0119840 | A1* | 5/2011 | Gardlik | .................... A61K 8/22 8/408 |

FOREIGN PATENT DOCUMENTS

| | | |
|---|---|---|
| DE | 10051774 A1 | 4/2002 |
| DE | 102005053850 A1 | 5/2007 |
| EP | 0778020 A1 | 6/1997 |
| EP | 1034777 A1 | 9/2000 |
| EP | 1174112 A2 | 1/2002 |
| EP | 1380287 A1 | 1/2004 |
| WO | 2005/072689 A1 | 8/2005 |
| WO | 2005115314 A1 | 12/2005 |
| WO | 2009134875 A2 | 11/2009 |

* cited by examiner

*Primary Examiner* — Jyothsna A Venkat
(74) *Attorney, Agent, or Firm* — James J. Cummings

(57) ABSTRACT

A combination of at least one selected dicarboxylic acid having 2 to 10 carbon atoms, in combination with at least one amino acid, selected from arginine, lysine, histidine or at least one of the salts of these amino acids, form a bleaching paste in order to reduce the damage to keratinic fibres caused by an oxidative bleaching treatment.

6 Claims, No Drawings

PASTE-LIKE BLEACHING AGENT AND METHOD FOR GENTLE OXIDATIVE HAIR LIGHTENING

FIELD OF THE INVENTION

The present invention generally relates to bleaching pastes which serve as agents for lightening keratinic fibres, in particular human hair. The present invention also relates to the use of a bleaching paste according to the invention for the gentle bleaching or oxidative lightening of human hair, and to a multi-component packaging unit (kit-of-parts) for lightening keratinic fibres, which includes a bleaching paste and, separately therefrom, an oxidizing agent preparation.

BACKGROUND OF THE INVENTION

Many consumers desire to lighten their own hair, as blond hair color is considered to be attractive and desirable from a fashion point of view. Various bleaching agents with different bleaching power are commercially available for this purpose. Oxidizing agents present in these products are capable of lightening hair fibres by oxidatively degrading the hair's own colorant, melanin. For a moderate bleaching effect, the use of hydrogen peroxide optionally with use of ammonia or other alkalizing agents—as sole oxidizing agent is sufficient. In order to attain a stronger bleaching effect, a mixture of hydrogen peroxide and at least one compound, selected from percarbonates and persalts, in particular peroxydisulfate salts and/or peroxymonosulfate salts, is usually used. To intensify the bleaching effect, the agents include higher use concentrations of hydrogen peroxide and percarbonates or persalts, in particular persulfates. Dark, dark brown, or black hair can thus be lightened by 4 to 6 shades in a single step. The hydrogen peroxide and the percarbonates or persalts are stored separately from one another until they are used so as not to prematurely deactivate the percarbonates or persalts. The hydrogen peroxide component, which comprises an aqueous solution of hydrogen peroxide, has an acidic pH value, in particular a pH value from 2.5 to 5.5, in particular from 3 to 5, measured in each case at 20° C., for stabilisation of the hydrogen peroxide.

For the melanin-degrading effect of the hydrogen peroxide and the bleaching effect on the keratinic fibres, it is advantageous however if the mixture to be used formed of hydrogen peroxide solution and persalt has an alkaline pH value, which preferably lies in the range from 8 to 12, particularly preferably in the range from 8.5 to 11.5, extremely preferably in the range from 9 to 10.5, measured in each case at 20° C.

There are a number of possibilities for setting an alkaline pH value of the lightening mixture to be used:
the bleaching paste, besides the at least one persalt or percarbonate, includes at least one alkalizing agent in such a total amount that the mixture to be used has the desired alkaline pH value; or
the hydrogen peroxide solution is not only combined with the bleaching paste, but additionally with an alkalizing agent preparation to form the mixture for use.

Bleaching pastes are suspensions of pulverulent persalts or percarbonates and optionally alkalizing agent(s), which are pulverulent, in an oil or an oil mixture which is substantially anhydrous and optionally thickened.

If the alkalizing agent preparation and/or the bleaching paste is/are mixed with oxidation dye precursor(s) and/or substantive dye(s), the hair can be colored at the same time. Corresponding 3-component hair dyes are offered in particular for consumers having very dark melanin-rich hair.

However, the lightening is also accompanied by damage to the hair, since not only the colors of the hair, but also the structural components of the hair are oxidatively damaged. Depending on the extent of the damage, it ranges from coarse, brittle and tangled hair, over a reduced resistance and tear resistance of the hair, to hair breakage. The greater the amount of the used hydrogen peroxide and optionally persalts or percarbonates, the greater generally is the damage therefore caused to the keratin fibres.

In order to minimize the damage to the hair and at least partially compensate for the damaging effect of the oxidizing agents, hair-lightening and hair-coloring agents including persalt(s) can be formulated with a higher content of oils. In the prior art, bleaching agent suspensions which constitute anhydrous suspensions of fine-particle persalts or percarbonates, solid at 25° C. and 1013 mbar, in an oil or an oil mixture, which can be thickened optionally with an oil-gelling agent, are described for example in EP 0778020, EP 1034777 EP 1380287 and WO 2009134875 A1.

WO 2005115314 A1 discloses a method for restructuring keratinic fibres in which the keratin fibres are brought into contact with cystine and with at least one dicarboxylic acid having 2 to 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid, and succinic acid is particularly preferred. DE 10051774 A1 describes the use of short-chain carboxylic acids having a molecular weight of less than 750 g/mol in cosmetic agents as active substance for restructuring keratinic fibres. EP 1174112 A discloses hair-treatment agents which, besides an organic acid, also include, as further obligatory constituents, an organic solvent, a cationic surfactant, and a higher alcohol and are used to repair pores in hair.

It is therefore desirable to provide agents for lightening or bleaching keratinic fibres, in particular human hair, which damage the keratin fibres to a minimal extent and which can be easily produced and handled. Furthermore, other desirable features and characteristics of the present invention will become apparent from the subsequent detailed description of the invention and the appended claims, taken in conjunction with this background of the invention.

BRIEF SUMMARY OF THE INVENTION

A first subject matter of the present invention is a bleaching paste, including
a) at least one oxidizing agent selected from sodium percarbonates and inorganic salts of a peroxysulfuric acid, and mixtures hereof,
b) also at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid and/or at least one salt of these acids and mixtures of these compounds, wherein the dicarboxylic acid having 2 to 10 carbon atoms is preferably selected from succinic acid, malic acid, maleic acid and the salts of succinic acid, malic acid or maleic acid,
c) also at least one amino acid, selected from arginine, lysine, histidine or at least one of the salts of these amino acids, d) at least one oil in a total amount of 16-60% by weight, preferably 20-50% by weight, particularly preferably 25-45% by weight, in each case in relation to the weight of the bleaching paste, and e) 0 to 4% by weight of water, in relation to the weight of the bleaching paste.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The terms keratin-containing or keratinic fibres are understood in accordance with the invention to mean furs, wool, feathers and in particular human hair. Although the agents according to the invention are primarily suitable for bleaching and/or lightening keratin-containing fibres, there is in principle nothing against a use also in other fields.

A suitable parameter for the quantification of the fibre damage, in particular hair damage, is the measurement of tensile strength (Young's modulus) of the keratin fibres.

The terms "paste" or "paste-like" are to be understood, in accordance with the invention, to mean an administration form which, at 20° C. and 1013 mbar, has a viscosity in the range of 200,000 to 1,600,000 mPas, preferably 250,000 to 1,400,00 mPas, particularly preferably 300,000 to 1,000,000 mPas, exceptionally preferably 400,000 to 750,000 mPas.

The paste viscosity is preferably determined by means of Brookfield; apparatus RVDV II+; spindle no. 96, 4 revolutions per minute, at 20° C.

Unless specified otherwise, all specified temperatures relate to a pressure of 1013 mbar.

The bleaching paste according to the invention includes, as first essential constituent, at least one oxidizing agent which is selected from sodium percarbonates and inorganic salts of a peroxysulfuric acid and mixtures thereof.

The term sodium percarbonates is understood to mean sodium carbonate-hydrogen peroxide complexes. Commercially conventional sodium percarbonate has the average composition $Na_2CO_3 \cdot 3H_2O_2$. Sodium percarbonate is present in the form of a white, water-soluble powder, which easily decays into sodium carbonate and "active" oxygen having a bleaching and oxidizing effect.

Peroxysulfuric acids are understood to mean peroxydisulfuric acid and peroxymonosulfuric acid (Caro's acid).

The at least one inorganic salt of a peroxysulfuric acid is preferably selected from ammonium peroxydisulfate, alkali metal peroxydisulfates, ammonium peroxymonosulfate, alkali metal peroxymonosulfates and alkali metal hydrogen peroxymonosulfates. Ammonium peroxydisulfate, potassium peroxydisulfate, sodium peroxydisulfate and potassium hydrogen peroxymonosulfate are particularly preferred. Within the scope of the works for the present invention, it has also proven to be particularly preferable if the bleaching paste according to the invention includes at least two different peroxydisulfates. Preferred peroxydisulfates are, here, combinations of ammonium peroxydisulfate and potassium peroxydisulfate and/or sodium peroxydisulfate.

Preferred bleaching pastes according to the invention include at least one oxidizing agent, which is selected from sodium percarbonates and inorganic salts of a peroxysulfuric acid and mixtures hereof, in a total amount of 2.5-65% by weight, preferably 10-60% by weight, more preferably 20-55% by weight, particularly preferably 25-50% by weight, and in particular 30-45% by weight, in each case in relation to the weight of the bleaching paste.

The bleaching paste according to the invention includes, as second essential constituent, also at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid and/or at least one salt of these acids and mixtures of these compounds, wherein the at least one dicarboxylic acid having 2 to 10 carbon atoms is preferably selected from succinic acid, malic acid and maleic acid and salts thereof.

Salts of dicarboxylic acids having 2 to 10 carbon atoms suitable in accordance with the invention are selected from the mono salts and di salts of the anions of succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid with ammonium ions, alkali metal ions, alkaline earth metal ions and the ions of basic amino acids, such as arginine, lysine and histidine, in particular of lithium, sodium, potassium, magnesium and calcium ions and mixtures of these salts.

Succinic acid, which is particularly preferred in accordance with the invention, has, at 1013 mbar, a melting point in the range of 185-187° C., i.e. is a solid at 20° C. Salts of succinic acid which are suitable in accordance with the invention are selected from the succinates and hydrogen succinates of ammonium ions, alkali metal ions, alkaline earth metal ions and the ions of basic amino acids, such as arginine, lysine and histidine, in particular of lithium, sodium, potassium, magnesium and calcium ions and mixtures of these salts. The specified salts of succinic acid can also include bound water of crystallization, in particular sodium succinate hexahydrate, which is particularly preferred in accordance with the invention.

Malic acid, which is particularly preferred in accordance with the invention, is optically active. Racemic DL-malic acid has, at 1013 mbar, a melting point in the range of 131-132° C., i.e. is a solid at 20° C. The enantiomers D-malic acid and L-malic acid each have, at 1013 mbar, a melting point in the range of 100-101° C. For cost reasons, racemic DL-malic acid is preferred.

Salts of malic acid suitable in accordance with the invention are selected from the malates and hydrogen malates of ammonium ions, alkali metal ions, alkaline earth metal ions, and the ions of basic amino acids, such as arginine, lysine and histidine, in particular of lithium, sodium, potassium, magnesium and calcium ions and mixtures of these salts, in particular disodium malate and dipotassium malate, but also calcium malate. The specified salts of malic acid suitable in accordance with the invention can include bound water of crystallization, in particular of disodium malate hemihydrate and disodium malate trihydrate.

Oxalic acid, which is preferred in accordance with the invention, has, at 1013 mbar, a melting point of 189.5° C. (anhydrous) or as dehydrate a melting point of 101.5° C. Salts of oxalic acid suitable in accordance with the invention are selected from the oxalates and hydrogen oxalates of ammonium ions, alkali metal ions, alkaline earth metal ions, in particular of lithium, sodium, potassium, magnesium and calcium ions and mixtures of these salts.

Malonic acid, which is preferred in accordance with the invention, has, at 1013 mbar, a melting point of 135° C. Salts of malonic acid suitable in accordance with the invention are selected from the malates and hydrogen malates of ammonium ions, alkali metal ions, alkaline earth metal ions, in particular of lithium, sodium, potassium, magnesium and calcium ions and mixtures of these salts.

Adipic acid, which is preferred in accordance with the invention, has, at 1013 mbar, a melting point of 152° C. Salts of adipic acid suitable in accordance with the invention are selected from the adipates and hydrogen adipates of ammonium ions, alkali metal ions and alkaline earth metal ions, in particular of lithium, sodium, potassium, magnesium and calcium ions and mixtures of these salts.

Pimelic acid, which is preferred in accordance with the invention, has, at 1013 mbar, a melting point of 105° C. Salts of pimelic acid suitable in accordance with the invention are selected from the pimelates and hydrogen pimelates of ammonium ions, alkali metal ions, and alkaline earth metal ions, in particular of lithium, sodium, potassium, magnesium and calcium ions, and mixtures of these salts.

Suberic acid, which is preferred in accordance with the invention, has, at 1013 mbar, a melting point of 144° C. Salts of suberic acid suitable in accordance with the invention are selected from the suberates and hydrogen suberates of ammonium ions, alkali metal ions, and alkaline earth metal ions, in particular of lithium, sodium, potassium, magnesium and calcium ions, and mixtures of these salts.

Azelaic acid, which is preferred in accordance with the invention, has, at 1013 mbar, a melting point of 106° C. Salts of azelaic acid suitable in accordance with the invention are selected from the azelates and hydrogen azelates of ammonium ions, alkali metal ions, and alkaline earth metal ions, in particular of lithium, sodium, potassium, magnesium and calcium ions, and mixtures of these salts.

Sebacic acid, which is preferred in accordance with the invention, has, at 1013 mbar, a melting point of 134.5° C. Salts of sebacic acid suitable in accordance with the invention are selected from the sebacates and hydrogen sebacates of ammonium ions, alkali metal ions, and alkaline earth metal ions, in particular of lithium, sodium, potassium, magnesium and calcium ions, and mixtures of these salts.

Maleic acid, which is particularly preferred in accordance with the invention, has, at 1013 mbar, a melting point of 130 to 131° C. (from ethanol or benzene) and of 138 to 139° C. (from water). Salts of maleic acid suitable in accordance with the invention are selected from the maleates and hydrogen maleates of ammonium ions, alkali metal ions, and alkaline earth metal ions, in particular of lithium, sodium, potassium, magnesium and calcium ions, and mixtures of these salts.

Fumaric acid, which is particularly preferred in accordance with the invention, has, at 1013 mbar, a melting point of 287° C. in a heat-sealed tube; fumaric acid sublimes at 200° C. Salts of fumaric acid suitable in accordance with the invention are selected from the fumarates and hydrogen fumarates of ammonium ions, alkali metal ions, and alkaline earth metal ions, in particular of lithium, sodium, potassium, magnesium and calcium ions, and mixtures of these salts.

D-tartaric acid (laevorotatory), which is particularly preferred in accordance with the invention, has, at 1013 mbar, a melting point of 168-170° C. Salts of D-tartaric acid suitable in accordance with the invention are selected from the tartrates and hydrogen tartrates of ammonium ions, alkali metal ions, and alkaline earth metal ions, in particular of lithium, sodium, potassium, magnesium and calcium ions, and mixtures of these salts.

L-tartaric acid (dextrorotatory), which is particularly preferred in accordance with the invention, has, at 1013 mbar, a melting point of 168-170° C. Salts of L-tartaric acid suitable in accordance with the invention are selected from the tartrates and hydrogen tartrates of ammonium ions, alkali metal ions, and alkaline earth metal ions, in particular of lithium, sodium, potassium, magnesium and calcium ions, and mixtures of these salts.

Meso-tartaric acid, which is particularly preferred in accordance with the invention, has, at 1013 mbar, a melting point of 140° C. Salts of meso-tartaric acid suitable in accordance with the invention are selected from the tartrates and hydrogen tartrates of ammonium ions, alkali metal ions, and alkaline earth metal ions, in particular of lithium, sodium, potassium, magnesium and calcium ions, and mixtures of these salts.

Racemic acid, which is particularly preferred in accordance with the invention, is the racemic mixture of D-tartaric acid and L-tartaric acid. Racemic acid has, at 1013 mbar, a melting point of 206° C. Salts of racemic acid suitable in accordance with the invention are selected from the tartrates and hydrogen tartrates of ammonium ions, alkali metal ions, and alkaline earth metal ions, in particular of lithium, sodium, potassium, magnesium and calcium ions, and mixtures of these salts.

Alpha-ketoglutaric acid, which is particularly preferred in accordance with the invention, has, at 1013 mbar, a melting point of 112-116° C. Salts of alpha-ketoglutaric acid suitable in accordance with the invention are selected from the alpha-ketoglutarates and alpha-keto hydrogen glutarates of ammonium ions, alkali metal ions, and alkaline earth metal ions, in particular of lithium, sodium, potassium, magnesium and calcium ions, and mixtures of these salts.

Beta-ketoglutaric acid, which is particularly preferred in accordance with the invention, has, at 1013 mbar, a melting point of 122° C.; it melts with decomposition. Salts of beta-ketoglutaric acid suitable in accordance with the invention are selected from the beta-ketoglutarates and beta-keto hydrogen glutarates of ammonium ions, alkali metal ions, and alkaline earth metal ions, in particular of lithium, sodium, potassium, magnesium and calcium ions, and mixtures of these salts.

Oxaloacetic acid, which is particularly preferred in accordance with the invention, has, at 1013 mbar, a melting point of 161° C. Salts of oxaloacetic acid suitable in accordance with the invention are selected from the oxaloacetates and oxalo hydrogen acetates of ammonium ions, alkali metal ions, and alkaline earth metal ions, in particular of lithium, sodium, potassium, magnesium and calcium ions, and mixtures of these salts.

Bleaching pastes which are preferred in accordance with the invention include the at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid and/or at least one salt of these acids, in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include succinic acid and/or at least one salt of succinic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include maleic acid and/or at least one salt of maleic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include fumaric acid and/or at least one salt of fumaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include oxalic acid and/or at least one salt of oxalic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include malonic acid and/or at least one salt of malonic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include adipic acid and/or at least one salt of adipic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include pimelic acid and/or at least one salt of pimelic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include suberic acid and/or at least one salt of suberic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include azelaic acid and/or at least one salt of azelaic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include sebacic acid and/or at least one salt of sebacic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include D-tartaric acid and/or at least one salt of D-tartaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include L-tartaric acid and/or at least one salt of L-tartaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include meso-tartaric acid and/or at least one salt of meso-tartaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include racemic acid and/or at least one salt of racemic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include alpha-ketoglutaric acid and/or at least one salt of alpha-ketoglutaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include beta-ketoglutaric acid and/or at least one salt of beta-ketoglutaric acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

Further bleaching pastes that are preferred in accordance with the invention include oxaloacetic acid and/or at least one salt of oxaloacetic acid in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste.

The bleaching paste according to the invention also includes, as third essential constituent, at least one amino acid selected from arginine, lystine, histidine or at least one of the salts of these amino acids. Mixtures of arginine and lysine are particularly preferred in accordance with the invention. The salts of arginine, lysine and histidine that are preferably suitable in accordance with the invention are the ammonium salts, alkali metal salts and alkaline earth metal salts, in particular the lithium, sodium, potassium, magnesium and calcium salts, in addition the hydrogen halides, in particularly the hydrochlorides, and mixtures of these salts. The amino acids suitable in accordance with the invention, selected from arginine, lysine, histidine and salts thereof, can also include water of crystallization.

Bleaching pastes that are preferred in accordance with the invention include at least one amino acid selected from arginine, lystine, histidine or at least one salt of these amino acids in a total amount, converted to the mass of free amino acid, of 0.1-7% by weight, preferably 0.2-5% by weight, particularly preferably 0.3-2.5% by weight, exceptionally preferably 1-2% by weight, in each case in relation to the weight of the bleaching paste.

The combination of succinic acid, lysine and arginine has proven to be exceptionally preferred in accordance with the invention. The combination of succinic acid and arginine is also exceptionally preferred. The combination of succinic acid and histidine is also exceptionally preferred.

Bleaching pastes that are particularly preferred in accordance with the invention include succinic acid and/or at least one succinic acid salt in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste, and also at least one amino acid, selected from arginine, lysine, histidine or at least one salt of these amino acids, in a total amount, converted to the mass of free amino acid, of 0.1-7% by weight, preferably 0.2-5% by weight, particularly preferably 0.3-2.5% by weight, exceptionally preferably 1-2% by weight, in each case in relation to the weight of the bleaching paste.

The combination of malic acid, lysine and arginine has proven to be exceptionally preferred in accordance with the invention. The combination of malic acid and arginine is also exceptionally preferred. The combination of malic acid and histidine is also exceptionally preferred.

Bleaching pastes that are particularly preferred in accordance with the invention include malic acid and/or at least one malic acid salt in a total amount, converted to the mass of free dicarboxylic acid, of 0.03-7% by weight, preferably 0.1-5% by weight, particularly preferably 0.5-3% by weight, exceptionally preferably 0.9-1.5% by weight, in each case in relation to the weight of the bleaching paste, and also at least one amino acid, selected from arginine, lysine, histidine or at least one salt of these amino acids, in a total amount, converted to the mass of free amino acid, of 0.1-7% by weight, preferably 0.2-5% by weight, particularly preferably 0.3-2.5% by weight, exceptionally preferably 1-2% by weight, in each case in relation to the weight of the bleaching paste.

The bleaching pastes according to the invention have a water content of 0 to 4% by weight, preferably 0.1 to 2% by weight, particularly preferably 0.2 to 0.7% by weight of water, in each case in relation to the weight of the bleaching paste. These values relate to the content of free water. What is not considered is the content of molecularly bound water or water of crystallization, which individual paste constituents may have.

The water content can be determined by means of Karl-Fischer titration, for example on the basis of ISO 4317 (version 2011-12).

Bleaching pastes according to the invention and that are preferred in accordance with the invention include at least one oil in a total amount of 16-60% by weight, preferably 20-50% by weight, particularly preferably 25-45% by weight, in each case in relation to the weight of the bleaching paste.

The at least one oil, which is included as carrier medium in the bleaching pastes according to the invention, is selected in particular from paraffin oil, silicone oil or ester oil and mixtures of these oils.

Further oils that are preferred in accordance with the invention are selected from natural and synthetic hydrocarbons, particularly preferably from paraffin oils, $C_{18}$-$C_{30}$ isoparaffins, in particular from isodecane, isotetradecane, and isohexadecane and mixtures thereof, and also 1,3-di-(2-ethylhexyl)-cyclohexane.

Further oils that are preferred in accordance with the invention are selected from the benzoic acid esters of linear or branched C8-C22 alkanols. Benzoic acid C12-C15 alkyl esters are particularly preferred.

Further oils that are preferred in accordance with the invention are selected from fatty alcohols having 6-30 carbon atoms, which are unsaturated or branched and saturated or branched and unsaturated. Preferred alcohol oils are 2-hexyldecanol, 2-octyldodecanol, 2-ethylhexyl alcohol, and isostearyl alcohol, and mixtures thereof.

Further cosmetic oils that are preferred in accordance with the invention are selected from the triglycerides (=triple esters of glycerol) of linear or branched, saturated or unsaturated, optionally hydroxylated C8-30 fatty acids. The use of natural oils, for example amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, blackcurrant seed oil, jojoba oil, linseed oil, macadamia nut oil, corn oil, almond oil, marula oil, evening primrose oil, olive oil, palm oil, palm kernel oil, para nut oil, pecan nut oil, peach kernel oil, rapeseed oil, castor oil, sea buckthorn pulp oil, sea buckthorn seed oil, sesame oil, soy oil, sunflower oil, grapeseed oil, walnut oil, wild rose oil, wheat germ oil, and the liquid components of coconut oil and the like, can be particularly preferred. Synthetic triglyceride oils are also preferred, however, in particular capric/caprylic triglycerides.

Further cosmetic oils that are particularly preferred in accordance with the invention are selected from the dicarboxylic acid esters of linear or branched $C_2$-$C_{10}$ alkanols, in particular diisopropyl adipate, di-n-butyl adipate, di-(2-ethylhexyl) adipate, dioctyl adipate, diethyl/di-n-butyl/dioctyl sebacate, dioctyl malate, dioctyl maleate, dicaprylyl maleate, diisooctyl succinate, di-2-ethylhexyl succinate, and di-(2-hexyldecyl)succinate.

Further cosmetic oils that are particularly preferred in accordance with the present invention are selected from esters of linear or branched, saturated or unsaturated fatty alcohols having 2-30 carbon atoms with linear or branched, saturated or unsaturated fatty acids having 2-30 carbon atoms, which can be hydroxylated. These include 2-hexyldecyl stearate, 2-hexyldecyl laurate, isodecyl neopentanoate, isononyl isononanoate, 2-ethylhexyl palmitate, and 2-ethylhexyl stearate, isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyl octanoic acid 2-butyl octanoate, diisotridecyl acetate, n-butyl stearate, n-hexyl laurate, n-decyl oleate, oleyl oleate, oleyl erucate, erucyl oleate, erucyl erucate, and ethylene glycol dioleate.

Further cosmetic oils that are preferred in accordance with the invention are selected from the addition products of 1 to 5 propylene oxide units with mono- or polyvalent C8-22 alkanols such as octanol, decanol, decanediol, lauryl alcohol, myristyl alcohol, and stearyl alcohol, e.g. PPG-2 Myristyl Ether and PPG-3 Myristyl Ether (Witconol® APM).

Further cosmetic oils that are preferred in accordance with the present invention are selected from addition products of at least 6 ethylene oxide and/or propylene oxide units with mono- or polyvalent $C_{3-22}$ alkanols such as glycerol, butanol, butanediol, myristyl alcohol, and stearyl alcohol, which can be esterified if desired, e.g. PPG-14 Butyl Ether (Ucon Fluid® AP), PPG-9 Butyl Ether (Breox® B25), PPG-10 Butanediol (Macol® 57), PPG-15 Stearyl Ether (Arlamol® E), and glycereth-7 diisononoate.

Further cosmetic oils that are preferred in accordance with the present invention are selected from $C_8$-$C_{22}$ fatty alcohol esters of monovalent or polyvalent $C_2$-$C_7$ hydroxycarboxylic acids, in particular the esters of glycolic acid, lactic acid, malic acid, tartaric acid, citric acid, and salicylic acid, for example $C_{12}$-$C_{15}$ alkyl lactate.

Further cosmetic oils that are preferred in accordance with the present invention are selected from symmetrical, asymmetrical, or cyclic esters of carbonic acid with $C_{3-22}$ alkanols, $C_{3-22}$ alkanediols, or $C_{3-22}$ alkanetriols, e.g. dicaprylyl carbonate (Cetiol® CC), or the esters according to the teaching of DE 19756454 A1, in particular glycerol carbonate.

Further cosmetic oils that are suitable in accordance with the present invention are selected from among the silicone oils that include, for example, dialkyl- and alkylarylsiloxanes such as cyclopentasiloxane, cyclohexasiloxane, dimethylpolysiloxane, and methyphenylpolysiloxane, but also hexamethyldisiloxane, octamethyltrisiloxane, and decamethyltetrasiloxane.

Mixtures of the aforementioned oils can be used exceptionally preferably in accordance with the invention.

Preferred bleaching pastes according to the invention are characterized in that the cosmetic oil is selected from natural and synthetic hydrocarbons, particularly preferably from paraffin oils, $C_{18}$-$C_{30}$ isoparaffins, in particular isoeicosane, polyisobutenes, and polydecenes, $C_8$-$C_{16}$ isoparaffins, and 1,3-di-(2-ethylhexyl)cyclohexane; benzoic acid esters of linear or branched $C_{8-22}$ alkanols; fatty alcohols having 6 to 30 carbon atoms, which are unsaturated or branched and saturated or branched and unsaturated; triglycerides of linear or branched, saturated or unsaturated, optionally hydroxylated $C_{8-30}$ fatty acids, in particular natural oils; dicarboxylic acid esters of linear or branched $C_2$-$C_{10}$ alkanols; esters of linear or branched, saturated or unsaturated fatty alcohols having 2-30 carbon atoms with linear or branched, saturated or unsaturated fatty acids having 2 to 30 carbon atoms, which can be hydroxylated; addition products of 1 to 5 propylene oxide units with mono- or polyvalent $C_{8-22}$ alkanols; addition products of at least 6 ethylene oxide and/or propylene oxide units with mono- or polyvalent $C_{3-22}$ alkanols; $C_8$-$C_{22}$ fatty alcohol esters of monovalent or polyvalent $C_2$-$C_7$ hydroxycarboxylic acids; symmetrical, asymmetrical, or cyclic esters of carbonic acid with $C_{3-22}$ alkanols, $C_{3-22}$ alkanediols, or $C_{3-22}$ alkanetriols; esters of dimers of unsaturated $C_{12}$-$C_{22}$ fatty acids (dimer fatty acids) with monovalent linear, branched, or cyclic $C_2$-$C_{18}$ alkanols or with polyvalent linear or branched $C_2$-$C_6$ alkanols; silicone oils; and mixtures of the aforementioned substances, preferably in a total amount of 16-60% by weight, particularly preferably 20-50% by weight, exceptionally preferably 25-45% by weight, in each case in relation to the weight of the bleaching paste.

Bleaching pastes that are preferred in accordance with the invention additionally include at least one inorganic alkalizing agent which is solid at 20° C. and 1013 mbar and which is included preferably in a total amount of 0.5-15% by weight, preferably 1-10% by weight, particularly preferably 2-8% by weight, exceptionally preferably 3-7% by weight, in each case in relation to the weight of the bleaching paste. Inorganic alkalizing agents that are particularly preferred in accordance with the invention and that are solid at 20° C. and 1013 mbar are selected from alkali metal silicates, alkaline earth metal silicates, alkaline earth metal hydroxide carbonates, alkaline earth metal carbonates, alkali metal metasilicates, alkaline earth metal metasilicates, alkali metal hydroxides, alkaline earth metal hydroxides, alkali (earth alkaline) metal phosphates and alkali (earth alkaline) metal hydrogen phosphates and mixtures of these substances. Inorganic alkalizing agents that are particularly preferred in accordance with the invention and that are solid at 20° C. and 1013 mbar are selected from sodium metasilicates having a molar $SiO_2/Na_2O$ ratio of 0.8-1.2, preferably of 0.9-1.1, exceptionally preferably of 1.

Bleaching pastes that are particularly preferred in accordance with the invention include, in each case in relation to their total weight, 0.5-15% by weight, preferably 1-10% by weight, particularly preferably 2-8% by weight, exceptionally preferably 3-7% by weight, in each case in relation to the weight of the bleaching paste, of sodium metasilicates having a molar $SiO_2/Na_2O$ ratio of 0.8-1.2, preferably of 0.9-1.1, exceptionally preferably of 1, as inorganic alkalizing agent that is solid at 20° C. and 1013 mbar.

In order to ensure the most uniform possible, storage-stable suspension of the obligatory constituents a), b) and c) and optionally further constituents which are insoluble in the carrier oil, bleaching pastes that are preferred in accordance with the invention include at least one substance which thickens the oil phase. Preferred thickening agents for the oil phase are selected from copolymer of C2-C4 alkene and styrene, linear saturated 1-alkanols having 12-30 carbon atoms, esters of saturated branched or unbranched alkane carboxylic acids having 12 to 24 C atoms, and saturated branched or unbranched alcohols having 16 to 50 C atoms, wherein the esters have a melting point in the range of 50° C. to 110° C., triglycerides of saturated and optionally hydroxylated $C_{12-30}$ fatty acids, wherein the triglycerides have a melting point in the range of 50° C. to 110° C., and mixtures of the aforementioned substances.

Bleaching pastes that are preferred in accordance with the invention include at least one substance which thickens the oil phase in a total amount of 1-15% by weight, preferably 2-10% by weight, particularly preferably 3-8% by weight, particularly preferably 4-6.5% by weight, in each case in relation to the weight of the bleaching paste.

Further bleaching pastes that are preferred in accordance with the invention include at least one substance which thickens the oil phase in a total amount of 1-15% by weight, preferably 2-10% by weight, particularly preferably 3-8% by weight, particularly preferably 4-6.5% by weight, in each case in relation to the weight of the bleaching paste, wherein the at least one substance which thickens the oil phase is selected from copolymers of C2-C4 alkene and styrene, linear saturated 1-alkanols having 12-30 carbon atoms, esters of saturated branched or unbranched alkane carboxylic acids having 12 to 24 C atoms, and saturated branched or unbranched alcohols having 16 to 50 C atoms, wherein the esters have a melting point in the range of 50° C. to 110° C., triglycerides of saturated and optionally hydroxylated $C_{12-30}$ fatty acids, wherein the triglycerides have a melting point in the range of 50° C. to 110° C., and mixtures of the aforementioned substances.

Copolymers of C2-C4 alkene and styrene that are preferred in accordance with the invention and that thicken the oil phase are included in bleaching pastes that are preferred in accordance with the invention in a total amount of 0.1-1.5% by weight, preferably 0.2-1% by weight, particularly preferably 0.3-0.8% by weight, exceptionally preferably 0.4-0.6% by weight, in each case in relation to the weight of the bleaching paste.

Copolymers of C2-C4 alkene and styrene that are preferred in accordance with the invention and that thicken the oil phase are selected from ethylene/propylene/styrene copolymers, butylene/ethylene/styrene copolymers, butylene/propylene/styrene copolymers, and mixtures of these copolymers.

The aforementioned copolymers of C2-C4 alkene and styrene preferably are not copolymers in which the monomer units are randomly distributed, but instead block copolymers, particularly preferably diblock copolymers and triblock copolymers. Such block copolymers have "hard" segments formed of polystyrene and "soft" segments formed of ethylene/propylene or ethylene/butylene or propylene/butylene. The individual blocks can comprise, here, 10 to 10000, preferably 50 to 5000, and in particular 100 to 500 monomers. Preferred diblock copolymers are styrene-ethylene propylene (S-EP) and styrene-ethylene butylene (S-EB); preferred triblock copolymers are styrene-ethylene propylene-styrene (S-EP-S) and styrene-ethylene butylene-styrene (S-EB-S). Mixtures of diblock and triblock copolymers are used with particular preference in accordance with the invention, wherein mixtures of styrene-ethylene propylene (S-EP) and styrene-ethylene propylene-styrene (S-EP-S) have proven to be particularly preferred. Here, the proportion of diblock copolymers very particularly preferably contributes to 10 to 90% by weight, and the proportion of triblock copolymers very particularly preferably contributes to 90 to 10% by weight, in each case in relation to the weight of the polymer mixture.

Bleaching pastes that are preferred in accordance with the invention include at least one copolymer of C2-C4 alkene and styrene which thickens the oil phase and which is selected from ethylene/propylene/styrene copolymers, butylene/ethylene/styrene copolymers, butylene/propylene/styrene copolymers, and mixtures of these copolymers in a total amount of 0.1-1.5% by weight, preferably 0.2-1% by weight, particularly preferably 0.3-0.8% by weight, exceptionally preferably 0.4-0.6% by weight, in each case in relation to the weight of the bleaching paste.

Bleaching pastes that are particularly preferred in accordance with the invention include a combination of ethylene/propylene/styrene copolymer and butylene/ethylene/styrene copolymer, particularly preferably in a total amount of 0.1-1.5% by weight, preferably 0.2-1% by weight, particularly preferably 0.3-0.8% by weight, exceptionally preferably 0.4-0.6% by weight, in each case in relation to the weight of the bleaching paste.

Linear saturated 1-alkanols having 12-30 carbon atoms which thicken the oil phase that are preferred in accordance with the invention are included in bleaching pastes that are preferred in accordance with the invention in a total amount of 0.1-10% by weight, preferably 0.5-8% by weight, particularly preferably 1-7% by weight, exceptionally preferably 2-5% by weight, in each case in relation to the weight of the bleaching paste.

Linear saturated 1-alkanols having 12-30 carbon atoms that are preferred in accordance with the invention are selected from lauryl alcohol, myristyl alcohol, cetyl alcohol, stearyl alcohol, arachidyl alcohol, and behenyl alcohol and also from mixtures of these 1-alkanols, particularly preferably from cetyl alcohol, stearyl alcohol and cetyl alcohol/stearyl alcohol mixtures.

Bleaching pastes that are particularly preferred in accordance with the invention include at least one linear saturated 1-alkanol having 12-30 carbon atoms, selected from lauryl alcohol, myristyl alcohol, cetyl alcohol, stearyl alcohol, arachidyl alcohol, and behenyl alcohol and also from mixtures of these 1-alkanols, particularly preferably from cetyl alcohol, stearyl alcohol and cetyl alcohol/stearyl alcohol mixtures, in a total amount of 0.1-10% by weight, preferably 0.5-8% by weight, particularly preferably 1-7% by weight, exceptionally preferably 2-5% by weight, in each case in relation to the weight of the bleaching paste.

Esters of saturated, branched or unbranched alkane carboxylic acids having 12 to 24 C atoms and saturated branched or unbranched alcohols having 16 to 50 C atoms having a melting point in the range of 50° C. to 110° C. that are preferred in accordance with the invention and that thicken the oil phase are included in bleaching pastes that are preferred in accordance with the invention in a total amount of 0.1-5% by weight, preferably 0.2-4% by weight, particularly preferably 0.3-2% by weight, exceptionally preferably 0.4-1% by weight, in each case in relation to the weight of the bleaching paste.

Esters of saturated, branched or unbranched alkane carboxylic acids having 12 to 24 C atoms and saturated branched or unbranched alcohols having 16 to 50 C atoms having a melting point in the range of 50° C. to 110° C. that are preferred in accordance with the invention and that thicken the oil phase are selected from $C_{16-36}$ alkyl stearates, in particular $C_{20}$-$C_{40}$ alkyl stearates, $C_{18-38}$ alkyl hydroxy stearoyl stearates, $C_{20-40}$ alkyl erucates, cetearyl behenate, cetyl behenate, stearyl behenate, and mixtures of these substances.

Triglycerides of saturated and optionally hydroxylated $C_{12-30}$ fatty acids having a melting point in the range of 50° C. to 110° C. that are preferred in accordance with the invention and that thicken the oil phase are included in bleaching pastes that are preferred in accordance with the invention in a total amount of 0.1-5% by weight, preferably 0.2-4% by weight, particularly preferably 0.3-2% by weight, exceptionally preferably 0.4-1% by weight, in each case in relation to the weight of the bleaching paste.

Triglycerides in the sense of the present invention are triesters of glycerol, i.e. esters, in which all OH groups of the glycerol are esterified with acid, in the present case with a saturated and optionally hydroxylated $C_{12-30}$ fatty acid.

Triglycerides of saturated and optionally hydroxylated $C_{12-30}$ fatty acids having a melting point in the range of 50° C. to 110° C. that are preferred in accordance with the invention and that thicken the oil phase are selected from hardened triglyceride fats, in particular hydrogenated palm oil, hydrogenated coconut oil, hydrogenated castor oil, glyceryl tribehenate (tribehenin) or glyceryl tri-12-hydroxystearate, as well as mixtures thereof. Hydrogenated castor oil, obtainable for example as commercial product Cutina® HR, is particularly preferred in accordance with the invention.

Bleaching pastes that are particularly preferred in accordance with the invention include at least one triglyceride of saturated and optionally hydroxylated $C_{12-30}$ fatty acids having a melting point in the range of 50° C. to 110° C., selected from hardened triglyceride fats, in particular hydrogenated palm oil, hydrogenated coconut oil, hydrogenated castor oil, glyceryl tribehenate (tribehenin) or glyceryl tri-12-hydroxystearate, as well as mixtures thereof, wherein hydrogenated castor oil is particularly preferred, in a total amount of 0.1-5% by weight, preferably 0.2-4% by weight, particularly preferably 0.3-2% by weight, exceptionally preferably 0.4-1% by weight, in each case in relation to the weight of the bleaching paste.

Bleaching pastes that are particularly preferred in accordance with the invention also include at least one or more hydrophilic thickeners preferably selected from polysaccharides which can be chemically and/or physically modified, acrylic acid homo- and copolymers, methacrylic acid homo- and copolymers, itaconic acid homo- and copolymers, and mixtures of these polymers. In particular, compounds from the group of polysaccharides are suitable as hydrophilic thickeners. Examples include representatives of the celluloses (cellulose itself and derivatives thereof), alginic acids (and their corresponding physiologically acceptable salts, the alginates), agar agar (with the polysaccharide agarose present as main constituent in agar agar), starch fractions and derivatives such as amylose, amylopectin and dextrins, karaya rubber, locust bean gum, gum arabic, dextrans, guar gum and xanthan gum.

Suitable cellulose derivatives are methyl celluloses, ethyl celluloses, hydroxyalkyl celluloses (such as hydroxyethyl cellulose), methylhydroxyalkyl celluloses, and carboxymethyl celluloses (such as those with the INCI name Cellulose Gum) and also their physiologically acceptable salts.

From the group of polysaccharides, anionic polysaccharides such as carboxymethyl celluloses, alginic acid and xanthan gum are preferably selected for the thickening of the agent according to the invention.

Carboxymethyl celluloses, alginic acids and xanthan gum, in addition to their physiologically acceptable salts, are referred to within the scope of the present invention as anionic polysaccharides, since the carboxylic acid groups present in these polysaccharides necessarily dissociate to a greater or lesser extent in water or aqueous formulation, whereby anionic carboxylate groups are formed, of which the number increases further with rising pH value.

In preferred embodiments, carboxymethyl cellulose (preferably carboxymethyl cellulose with the INCI name Cellulose Gum) is included as hydrophilic thickener in view of a reliable viscosity adjustment and residue-free application to keratin fibres and the scalp. Carboxymethyl cellulose can be included in a preferred embodiment as the sole hydrophilic thickener. However, in particular a combination of carboxymethyl cellulose and xanthan (preferably xanthan with the INCI name Xanthan Gum) or physiologically acceptable salts thereof is also preferred.

The physiologically acceptable salts are understood to mean in particular the sodium salts, but also the potassium salts, and also magnesium and calcium salts.

Bleaching pastes that are particularly preferred in accordance with the invention include at least one hydrophilic thickener in a total amount of 0.1 to 5% by weight, preferably of 0.5 to 4% by weight, more preferably of 1 to 3% by weight, and very particularly preferably of 1.7 to 2.5% by weight, in each case in relation to the weight of the bleaching paste.

In a further preferred embodiment of the present invention The bleaching paste according to the invention includes, in each case in relation to the weight of the paste, 0.1 to 3% by weight, preferably 0.5 to 2.5% by weight, more preferably 1 to 2% by weight, even more preferably 1 to 1.5% by weight of carboxymethyl cellulose.

In a further preferred embodiment of the present invention the bleaching paste according to the invention includes, in each case in relation to the weight of the paste, 0.1 to 3% by weight, preferably 0.5 to 2.5% by weight, more preferably 1 to 2% by weight, even more preferably 1 to 1.5% by weight of xanthan.

Hydrophilic thickeners that are suitable in accordance with the invention include acrylic acid homo- and copolymers, methacrylic acid homo- and copolymers, itaconic acid homo- and copolymers, preferably selected from the group formed by the crosslinked and uncrosslinked homo- or copolymers of acrylic acid, methacrylic acid and salts thereof and alkyl esters, homo- or copolymers of acrylic acid amides and/or methacrylic acid amides, copolymers of acrylic acid and acrylic acid amides and mixtures thereof, copolymers of ethoxylated C1-C6 alkyl esters of methacrylic acid and the sulfonated acrylic acid amides and salts thereof and crosslinked copolymers of methacrylic acid, acrylic acid amides and the sulfonated acrylic acid amides and salts thereof. The above-mentioned polymers and copolymers can be crosslinked or uncrosslinked. Provided the above-mentioned polymers and copolymers do not have any alkyl groups with a chain length of at least 8 carbon atoms, they are preferably crosslinked. Provided the above-mentioned polymers and copolymers have alkyl groups with a chain length of at least 8 carbon atoms, they are preferably uncrosslinked.

Examples of polymers that are preferred as hydrophilic thickeners are those known for example under the INCI name Copolymer Ammonium Acryloyldimethyltaurate/Beheneth-25 methacrylate Crosspolymer (trade name: Aristoflex HMB; Clariant), the copolymers known under the INCI name Acrylates/C10-30 Alkyl Acrylate Crosspolymer, and the crosslinked copolymer known under the INCI name Polyacrylate Crosspolymer-11 (trade name: Aristoflex Velvet; Clariant).

In addition, bleaching pastes that are preferred in accordance with the invention include one or more alkoxylated fatty alcohols, in particular ethoxylated fatty alcohols. In particular, fatty alcohols having 12 to 80 ethylene oxide groups, preferably 25 to 50 ethylene oxide groups, are suitable. Ethoxylated fatty alcohols that are suitable in accordance with the invention are those of the following formula (FAEO):

$$RO[CH_2CH_2-O]_nH \quad\quad\quad (FAEO)$$

in which R stands for an unbranched or branched, saturated or unsaturated C10-C24 alkyl group and n stands for an integer from 12 to 80. R preferably stands for an unbranched, saturated C12-C18 alkyl group or for an unbranched, monounsaturated C12-C18 alkyl group. In the formula (FAEO), n preferably stands for an integer from 20 to 60, and n particularly preferably stands for an integer from 25 to 50. Examples of alkoxylated fatty alcohols of the formula (FAEO) are Laureth-20, Laureth-25, Laureth-30, Laureth-40, Laureth-50, Myreth-20, Myreth-25, Myreth-30, Myreth-40, Myreth-50, Ceteth-20, Ceteth-25, Ceteth-30, Ceteth-40, Ceteth-50, Steareth-20, Steareth-25, Steareth-30, Steareth-40, Steareth-50, Ceteareth-20, Ceteareth-25, Ceteareth-30, Ceteareth-40, Ceteareth-50, Oleth-20, Oleth-25, Oleth-30, Oleth-40 and Oleth-50.

Bleaching pastes that are particularly preferred in accordance with the invention include one or more alkoxylated fatty alcohols, in particular ethoxylated fatty alcohols of the above formula (FAEO) in a total amount of 0.2 to 13.0% by weight, preferably 2.0 to 8.0% by weight, more preferably of 3.0 to 7.0% by weight, in each case in relation to the weight of the bleaching paste according to the invention.

Bleaching pastes that are particularly preferred in accordance with the invention include Ceteareth-30 and/or Ceteareth-50 or a combination thereof. In particular, a combination of Ceteareth-30 and Ceteareth-50 is preferred. Here, Ceteareth-30 is preferably included in an amount of 0.1 to 5% by weight, more preferably 0.2 to 1% by weight, even more preferably 0.3 to 0.7% by weight, and Ceteareth-50 is preferably included in an amount of 0.1 to 8% by weight, more preferably 2 to 6% by weight, even more preferably 3 to 5% by weight, in each case in relation to the weight of the bleaching paste according to the invention. It has been found that particularly advantageous properties of the bleaching pastes that are particularly preferred in accordance with the invention and of the mixtures for use produced therefrom are attained with an amount of Ceteareth-30 and Ceteareth-50 in the specified ranges, in particular with a combination of Ceteareth-30 and Ceteareth-50.

A further subject of the present invention is a method for lightening keratinic fibres, in particular human hair, in which a bleaching paste according to the invention or a bleaching paste that is preferred in accordance with the invention is mixed with an oxidation composition which, in each case in relation to its weight, includes 50-96% by weight, preferably 70-93% by weight, particularly preferably 80-90% by weight of water and 0.5-20% by weight of hydrogen peroxide and also includes at least one pH adjuster in such an amount that the oxidation composition has a pH value in the range of 2.5 to 5.5 at 20° C., is applied directly thereafter to the keratin-containing fibres, is left on the fibres for 5 to 60 minutes, and then the fibres are rinsed with water and the bleaching paste is optionally washed out using a surfactant-containing cleansing agent, wherein the bleaching paste (B) and the oxidation composition (Ox) are preferably mixed with one another in a weight-based ratio (B):(Ox) of 0.2-1, particularly preferably 0.3-0.8, more preferably 0.4-0.7, exceptionally preferably 0.5-0.6.

The oxidation composition (Ox) used in the lightening method according to the invention includes fundamentally water and hydrogen peroxide. The concentration of hydrogen peroxide is determined on the one hand by the legal requirements and on the other hand by the desired effect. It is 0.5-20% by weight, preferably 3-12% by weight, particularly preferably 6-9% by weight of hydrogen peroxide (calculated as 100% $H_2O_2$), in each case in relation to the weight of the oxidation composition (Ox).

The oxidation composition (Ox), in order to stabilise the hydrogen peroxide, preferably has an acidic pH value, in particular a pH value in the range of 2.5 to 5.5, measured at 20° C. To stabilise the hydrogen peroxide, complexing agents, preservatives and/or buffer substances are also preferably included.

The bleaching paste that is preferred in accordance with the invention is of such a composition that the mixture with the aforementioned oxidation composition (Ox), i.e. the color-changing agent ready for use, in particular bleaching agent, has an alkaline pH value, preferably a pH value of 8 to 11.5, particularly preferably a pH value of 8.5 to 11, exceptionally preferably a pH value of 9.0 to 10.5, in each case measured at 20° C.

Oxidation compositions (Ox) used particularly preferably in accordance with the invention also include at least one oil and/or at least one fatty component having a melting point in the range of 23-110° C., preferably in a total amount of 0.1-60% by weight, particularly preferably 0.5-40% by weight, exceptionally preferably 2-24% by weight, in each case in relation to the weight of the oxidation composition (Ox) used with particular preference in accordance with the invention. The oils suitable for the oxidation compositions (Ox) preferably used in accordance with the invention are the same oils as those disclosed above as being a suitable carrier medium for the bleaching pastes.

Fatty components preferably used in accordance with the invention in the oxidation compositions (Ox) with a melting point in the range of 23-110° C. are selected from linear saturated 1-alkanols with 12-30 carbon atoms, preferably in a total amount of 0.1-8% by weight, particularly preferably 2.0 to 6.0% by weight, in each case in relation to the weight of the oxidation composition (Ox) used in accordance with the invention.

The at least one linear saturated 1-alkanol having 12-30 carbon atoms is preferably selected from lauryl alcohol, myristyl alcohol, cetyl alcohol, stearyl alcohol, arachidyl alcohol, and behenyl alcohol and also from mixtures of these 1-alkanols, particularly preferably from cetyl alcohol, stearyl alcohol and cetyl alcohol/stearyl alcohol mixtures.

Oxidation compositions (Ox) that are used with preference in accordance with the invention also include, in each case in relation to their weight, a total amount of 0.1-8% by weight, preferably in a total amount of 2-6% by weight, wherein at least one 1-alkanol is included, selected from cetyl alcohol, stearyl alcohol and cetyl alcohol/stearyl alcohol mixtures.

Further oxidation compositions (Ox) that are used with preference in accordance with the invention include at least one fatty component having a melting point in a range of 23-110° C., which is selected from esters of a saturated, monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which can be hydroxylated, candelilla wax, carnauba wax, beeswax, saturated linear $C_{14}$-$C_{36}$ carboxylic acids, and mixtures of the aforementioned substances.

Further oxidations compositions (Ox) that are preferably used in accordance with the invention include at least one surfactant or at least one emulsifier, preferably in a total amount of 0.5-10% by weight, preferably 1-5% by weight, in each case in relation to the weight of the oxidation composition (Ox) used in accordance with the invention.

Surfactants and emulsifiers in the sense of the present invention are amphiphilic (bifunctional) compounds that consist of at least one hydrophobic and at least one hydrophilic molecule part. The hydrophobic group is preferably a hydrocarbon chain having 8-28 carbon atoms, which can be saturated or unsaturated, linear or branched. This $C_8$-$C_{28}$ alkyl chain is particularly preferably linear. The basic properties of the surfactants and emulsifiers are oriented absorption at boundary surfaces and also the aggregation to micelles and the formation of lyotropic phases.

Anionic, non-ionic and cationic surfactants are particularly suitable in accordance with the invention. However, zwitterionic and amphoteric surfactants are also very suitable in accordance with the invention.

All anionic surface-active substances that are suitable for use on the human body are suitable as anionic surfactants in the compositions according to the invention. These are characterized by a water-soluble-making anionic group, such as a carboxylate, sulfate, sulfonate or phosphate group and a lipophilic alkyl group having 8 to 30 C atoms. In addition, glycol or polyglycolether groups, ester, ether and amide groups and also hydroxyl groups can be included in the molecule. Examples of suitable anionic surfactants are linear and branched fatty acids having 8 to 30 C atoms (soaps), alkylether carboxylic acids, acyl sarcosides, acyl taurides, acyl isethionates, sulfosuccinic acid monoesters and dialkylesters and sulfosuccinic acid mono-alkylpolyoxyethyl esters, linear alkane sulfonates, linear alpha-olefin sulfonates, alkylsulfates and alkylether sulfates and also alkyl and/or alkenyl phosphates. Preferred anionic surfactants are alkyl sulfates, alkylether sulfates and alkylether carboxylic acids each having 10 to 18 C atoms, preferably 12 to 14 C atoms in the alkyl group and up to 12 glycolether groups, preferably 2 to 6 glycol ether groups in the molecule.

Examples of such surfactants are the compounds with the INCI names Sodium Laureth Sulfate, Sodium Lauryl Sulfate, Sodium Myreth Sulfate or Sodium Laureth Carboxylate.

Surface-active compounds that carry, in the molecule, at least one quaternary ammonium group and at least one carboxylate, sulfonate or sulfate groups are referred to as zwitterionic surfactants. Particularly suitable zwitterionic surfactants are what are known as betaines, such as the N-alkyl-N,N-dimethylammonium glycinates, for example coco-alkyl-dimethylammonium glycinate, N-acyl-aminopropyl-N,N-dimethylammonium glycinates, for example coco-acylaminopropyl-dimethylammonium glycinate, and 2-alkyl-3-carboxymethyl-3-hydroxyethyl imidazoline each having 8 to 18 C atoms in the alkyl or acyl group and also coco-acylaminoethylhydroxyethylcarboxymethyl glycinate. A preferred zwitterionic surfactant is the fatty acid amide derivative known under the INCI name Cocamidopropyl Betaine.

Amphoteric surfactants are understood to be surface-active compounds which, in addition to a $C_8$-$C_{24}$ alkyl or acyl group, also include at least one free amino group and at least one —COOH— or –$SO_3H$ group in the molecule and are capable of forming inner salts. Examples of suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkyl aminopropionic acids, and alkyl amino acetic acids each having 8 to 24 C atoms in the alkyl group. Particularly preferred amphoteric surfactants are N-coco-alkylaminopropionate, coco-acylaminoethylaminopropionate, and $C_{12}$-$C_{18}$ acyl sarcosine.

Non-ionic surfactants include, as hydrophilic group, for example a polyol group, a polyalkylene glycol ether group or a combination of polyol group and polyglycol ether group. Such compounds are, for example, addition products of 4 to 50 mol ethylene oxide and/or 0 to 5 mol propylene oxide with linear and branched fatty alcohols, with fatty acids, and with alkyl phenols, in each case having 8 to 20 C atoms in the alkyl group, ethoxylated mono-, di- and tri-glycerides, such as glycerol monolaurate+20 ethylene oxide with sorbitol fatty acid ester, such as Polysorbate (Tween 20, Tween 21, Tween 60, Tween 61, Tween 81), addition products of ethylene oxide with fatty acid alkanolamides and fatty amines, and alkylpolyglycosides. In particular, $C_8$-$C_{22}$ alkylmono- and -oligoglycosides and ethoxylated analogues thereof and also ethylene oxide addition products with saturated or unsaturated linear fatty alcohols each having 2 to 30 mol ethylene oxide per mol of fatty alcohol are suitable as non-ionic surfactants.

Further oxidation compositions used with preference in accordance with the invention are characterized in that the at least one anionic surfactant is selected from alkyl sulfates, alkyl ether sulfates, and alkyl ether carboxylic acids each having 10 to 18 C atoms, preferably 12 to 14 C atoms in the alkyl group and up to 12 glycolether groups, preferably 2 to 6 glycol ether groups, in the molecule.

Further oxidation compositions used with preference in accordance with the invention are characterized in that at least one non-ionic surfactant, selected from ethylene oxide addition products with saturated or unsaturated linear fatty alcohols each having 2 to 30 mol of ethylene oxide per mol of fatty alcohol, and at least one anionic surfactant, selected from alkyl sulfates, alkylether sulfates, and alkyl ether carboxylic acids, each having 10 to 18 C atoms, preferably 12 to 14 C atoms, in the alkyl group and up to 12 glycol ether groups, preferably 2 to 6 glycol ether groups, in the molecule are included, wherein the ratio by weight of the totality of all anionic surfactants to the totality of all non-ionic surfactants particularly preferably lies in the range of 5-50, preferably 10-30.

All cationic surface-active substances that are suitable for use on the human body are suitable in principle as cationic surfactants in oxidation compositions (Ox) used with preference in accordance with the invention. These are characterized by at least one water-soluble-making cationic group, such as a quaternary ammonium group, or by at least one water-soluble-making cationisable group, such as an amine group, and also at least one (lipophilically acting) alkyl group having 6 to 30 C atoms or at least one (lipophilically acting) imidazole group or at least one (lipophilically acting) imidazyl alkyl group.

Oxidation compositions (Ox) used with particular preference in accordance with the invention include at least one cationic surfactant, which is preferably selected from quaternary ammonium compounds having at least one C8-C24 alkyl group, esterquats and amidoamines each having at least one C8-C24 acyl group and mixtures hereof. Preferred quaternary ammonium compounds having at least one C8-C24 alkyl group are ammonium halides, in particular chlorides and ammonium alkyl sulfates, such as methosulfates or ethosulfates, such as C8-C24 alkyl trimethyl ammonium chlorides, C8-C24 dialkyl dimethyl ammonium chlorides and C8-C24 trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride, and tricetyl methyl ammonium chloride, and the imidazolium compounds known under the INCI names Quaternium-27, Quaternium-83, Quaternium-87 and Quaternium-91. The alkyl chains of the above-mentioned surfactants preferably have 8 to 24 carbon atoms. Esterquats are cationic surfactants which include both at least one ester function and at least one quaternary ammonium group as structural element and also at least one C8-C24 alkyl group or C8-C24 acyl group. Preferred esterquats are quaternised ester salts of fatty acids with triethanolamine, quaternised ester salts of fatty acids with diethanol alkylamines and quaternised ester salts of fatty acids with 1,2-dihydroxypropyldialkylamines. Such products are sold for example under the trade name Stepantex®, Dehyquart® and Armocare®. N,N-Bis(2-Palmitoyloxyethyl)dimethylammonium chloride, Distearylethyl Dimonium Methosulfate and Distearoylethyl Hydroxyethylmonium Methosulfate are preferred examples of such esterquats.

The alkyl amidoamines are usually produced by amidation of natural or synthetic C8-C24 fatty acids and fatty acid sections with di-(C1-C3)alkyl amino amines. A compound from this substance group which is particularly suitable in accordance with the invention is stearamidopropyl dimethylamine.

Oxide compositions (Ox) used with particular preference in accordance with the invention include at least one cationic surfactant in a total amount of 0.01-5% by weight, preferably 0.1-3% by weight, particularly preferably 0.3-2% by weight, in each case in relation to the weight of the oxidation composition (Ox) used in accordance with the invention.

A further subject of the present invention is a multi-component packaging unit (kit-of-parts) for lightening keratinic fibres which includes at least two components packaged separately from one another and which is characterized in that i) the first component (I) is a bleaching paste according to the invention or is a bleaching paste that is preferred in accordance with the invention, ii) the second component (II) is an oxidation composition which includes, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C., wherein components (I) and (II) are preferably present in a weight-based ratio to one another (I):(II) of 0.2-1, particularly preferably 0.3-0.8, more preferably 0.4-0.7, exceptionally preferably 0.5-0.6.

A further subject of the present invention is a multi-component packaging unit (kit-of-parts) for changing the color of keratinic fibres, in particular human hair, including at least three components packaged separately from one another, wherein i) the first component (I) is a bleaching paste according to the invention or is a bleaching paste that is preferred in accordance with the invention, ii) the second component (II) is an oxidation composition which includes, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C., iii) the third component (III) is an alkalizing composition (Alk) which includes water and at least one alkalizing agent, which is selected from ammonia, alkanolamines and mixtures hereof and has a pH value in the range of 8-12, preferably of 9-11, particularly preferably of 9.5-10.5, in each case measured at 20° C., wherein the bleaching paste (B), the oxidation composition (Ox) and the alkalizing composition (Alk) are preferably present in a weight-based ratio to one another (B):(Ox):(Alk) of (0.7-1.3):(2-3):(2-3), particularly preferably (0.8-1.2):(2.3-2.7):(2.3-2.7).

A further subject of the present invention is a multi-component packaging unit (kit-of-parts) for changing the color of keratinic fibres, in particular human hair, including at least three components packaged separately from one another, wherein i) the first component (I) is a bleaching paste according to the invention or is a bleaching paste that is preferred in accordance with the invention, ii) the second component (II) is an oxidation composition which includes, in each case in relation to its weight, 50-96% by weight, preferably 70-93% by weight, particularly preferably 80-90% by weight of water and 0.5-20% by weight of hydrogen peroxide and has a pH value in the range of 2.5 to 5.5, measured at 20° C., iii) the third component (III) is an alkalizing composition (Alk) which includes water and at least one alkalizing agent, which is selected from ammonia, alkanolamines and mixtures hereof and has a pH value in the range of 8-12, preferably of 9-11, particularly preferably of 9.5-10.5, in each case measured at 20° C., wherein the bleaching paste (B), the oxidation composition (Ox) and the alkalizing composition (Alk) are preferably present in a weight-based ratio to one another (B):(Ox):(Alk) of (0.7-1.3):(2-3):(2-3), particularly preferably (0.8-1.2):(2.3-2.7):(2.3-2.7), exceptionally preferably 1:2:2.

A multi-component packaging unit comprises a plurality of individual components which are packaged separately from one another, and also a common packaging for these components, for example a collapsible box. The components are provided therein, each separated into different containers. Within the scope of the present invention, a container is understood to mean a wrapping which is present in the form of an optionally re-closable bottle, a tube, a tin, a bag, a sachet or a similar wrapping. In accordance with the invention, the wrapping material is not subject to any limitations. However, the wrappings are preferably made of plastic.

In addition, the packaging unit can comprise application aids, such as combs, hairbrushes or paintbrushes, personal protective clothing, in particular disposable gloves, and a set of instructions.

In a further preferred embodiment of the invention a bleaching paste according to the invention or a bleaching paste that is preferred in accordance with the invention can be combined with an alkalizing composition and with an oxidation composition to form a lightening, color-changing agent for keratinic fibres.

Since, when treating keratinic fibres, in particular hair, with oxidizing agents, in particular with hydrogen peroxide, the dye melanin, which occurs naturally in the fibres, is destroyed to a certain extent, the fibres/hair are/is inevitably lightened, i.e. the color thereof changes even without the presence of a dye. The term "color change" in the sense of the present invention therefore includes both the lightening and coloring using one or more dyes.

The alkalizing composition (Alk) used in accordance with the invention includes water and at least one alkalizing agent, which is selected from ammonia, alkanolamines and mixtures hereof and has a pH value in the range of 8-12, preferably 9-11, particularly preferably 9.5-10.5, in each case measured at 20° C. Preferred alkanolamines are selected from monoethanolamine, 2-amino-2-methylpropanol and triethanolamine and also mixtures hereof, wherein monoethanolamine is particularly preferred. An exceptionally preferred alkalizing agent is ammonia.

Ammonia ($NH_3$) in the form of its aqueous solution is usually used. Aqueous ammonia solutions include ammonia ($NH_3$) often in concentrations of 10 to 32% by weight. Here, the use of an aqueous ammonia solution which includes 25% by weight ammonia ($NH_3$) is preferred.

Besides ammonia and alkanolamines, at least one further alkalizing agent can be included, which is selected from alkali metal silicates, alkaline earth metal silicates, alkaline earth metal hydroxide carbonates, alkaline earth metal carbonates, alkali metal metasilicates, alkaline earth metal metasilicates, alkali metal hydroxides, alkaline earth metal hydroxides and mixtures of these substances. Ammonia and/or monoethanolamine are preferably included in the alkalizing compositions used with preference in accordance with the invention in amounts of 0.01-10% by weight, preferably of 0.1-7.5% by weight, more preferably of 0.5-5.5% by weight, and particularly preferably of 1.5-4.5% by weight, in each case in relation to the weight of the alkalizing composition.

A further subject of the present invention is a method for changing the color of keratinic fibres, in particular human hair, in which a bleaching paste according to the invention or a bleaching paste that is preferred in accordance with the invention is mixed with an oxidation composition (Ox) which includes, in each case in relation to its weight, 50-96% by weight, preferably 70-93% by weight, particularly preferably 80-90% by weight of water and 0.5-20% by weight of hydrogen peroxide and also includes at least one pH adjuster in such an amount that the oxidation composition has a pH value in the range of 2.5 to 5.5, measured at 20° C., and additionally is mixed with an alkalizing composition (Alk) which includes water and at least one alkalizing agent which is selected from ammonia, alkanolamines and mixtures hereof and has a pH value in the range of 8-12, preferably 9-11, particularly preferably of 9.5-10.5, in each case measured at 20° C.,
is applied to the keratin-containing fibres directly thereafter, is left on the fibres for 5 to 60 minutes, and the fibres are then rinsed with water and the bleaching paste is optionally washed out using a surfactant-containing cleansing agent, wherein the bleaching paste (B), the oxidation composition (Ox), and the alkalizing composition (Alk) are preferably mixed with one another in a weight-based ratio (B):(Ox):(Alk) of (0.7-1.3):(2-3):(2-3), particularly preferably (0.8-1.2):(2.3-2.7):(2.3-2.7), exceptionally preferably 1:2:2.

In accordance with the invention, the bleaching paste is preferably composed such that the mixture with the aforementioned oxidation composition (Ox) and with the aforementioned alkalizing composition (Alk), i.e. the color-changing agent ready for use, in particular the bleaching agent, has an alkaline pH value, preferably a pH value from 8 to 11.5, particularly preferably a pH value from 8.5 to 11, exceptionally preferably a pH value from 9.0 to 10.5, in each case measured at 20° C.

The ready-for-use mixtures of a bleaching paste according to the invention or a bleaching paste that is preferred in accordance with the invention with one of the aforementioned oxidation compositions (Ox) and optionally with one of the aforementioned alkalizing compositions (Alk) preferably have a viscosity in the range of 3000 to 20000 mPas, particularly preferably 6000 to 15000 mPas, in each case measured at 20° C. using a Haake cylinder/cylinder viscometer, SV I rotary/measurement system with a cooling time of 5 minutes. In this measurement method the viscosity value is determined at a shear rate of 1/7.2 s. The measurement program operates with the ramp of 0-1/60 s. A viscosity in this range means that the ready-for-use agent can be easily applied and also has such a flow behaviour that this guarantees, for the agent, a sufficiently long time of action at the site of action on the keratinic fibres.

In order to facilitate the miscibility of the alkalizing composition used in accordance with the invention with the bleaching paste according to the invention or the bleaching paste preferred in accordance with the invention and the oxidation composition used in accordance with the invention and so as to also improve the use properties of the resultant mixture that is to be used, the alkalizing composition used with preference in accordance with the invention preferably includes, in each case in relation to its weight, at least one surfactant in a total amount of 0.5-10% by weight, preferably 2-8% by weight.

The surfactants suitable for the alkalizing compositions (Alk) used with preference in accordance with the invention are selected from the same anionic, cationic, non-ionic, amphoteric and zwitterionic surfactants and emulsifiers disclosed further above as surfactants and emulsifiers suitable for the oxidation compositions (Ox) used with preference.

Alkalizing compositions (Alk) that are used with particular preference in accordance with the invention also include at least one oil and/or at least one fat component having a melting point in the range of 23-110° C., preferably in a total amount of 0.1-60% by weight, particularly preferably 0.5-40% by weight, exceptionally preferably 2-24% by weight, in each case in relation to the weight of the alkalizing composition (Alk) used with preference in accordance with the invention. The oils suitable for the alkalizing compositions (Alk) used with preference in accordance with the invention are the same oils disclosed further above as suitable carrier medium for the bleaching paste.

Fat components having a melting point in the range of 23-110° C. and used with preference in the alkalizing compositions (Alk) in accordance with the invention are selected from linear saturated 1-alkanols having 12-30 carbon atoms, preferably in a total amount of 0.1-20% by weight, particularly preferably 3-15% by weight, exceptionally preferably 5-10% by weight, in each case in relation to the weight of the alkalizing composition used in accordance with the invention.

The at least one linear saturated 1-alkanol having 12-30 carbon atoms is preferably selected from lauryl alcohol, myristyl alcohol, cetyl alcohol, stearyl alcohol, arachidyl alcohol, and behenyl alcohol and also from mixtures of these 1-alkanols, particularly preferably from cetyl alcohol, stearyl alcohol and cetyl alcohol/stearyl alcohol mixtures.

Alkalizing compositions (Alk) used with preference in accordance with the invention also include, in each case in relation to their weight, at least one linear saturated 1-alkanol having 12-30 carbon atoms in a total amount of 0.1-20% by weight, preferably in a total amount of 3-15% by weight, exceptionally preferably 5-10% by weight, wherein at least one 1-alkanol, selected from cetyl alcohol, stearyl alcohol and cetyl alcohol/stearyl alcohol mixtures, is included.

Further alkalizing compositions (Alk) used with preference in accordance with the invention include at least one fat component having a melting point in the range of 23-110° C., which is selected from esters of a saturated monovalent $C_{16}$-$C_{60}$ alkanol and a saturated $C_8$-$C_{36}$ monocarboxylic acid, in particular cetyl behenate, stearyl behenate and $C_{20}$-$C_{40}$ alkyl stearate, glycerol triesters of saturated linear $C_{12}$-$C_{30}$ carboxylic acids, which can be hydroxylated, candelilla wax, carnauba wax, beeswax, saturated linear $C_{14}$-$C_{36}$ carboxylic acids, and mixtures of the aforementioned substances.

The bleaching pastes according to the invention or the bleaching pastes that are preferred in accordance with the invention and/or the alkalizing compositions used with preference in accordance with the invention can also include at least one substantive dye. These are dyes which are drawn directly onto the hair and do not require an oxidizing process to form the color. To dull undesirable residual color impressions caused by melanin degradation products, in particular in the red or blue spectrum, certain substantive dyes of the complementary colors are particularly preferably included. Substantive dyes are usually nitrophenylenediamines, nitroaminophenols, azo dyes, anthraquinones or indophenols. Substantive dyes are known as anionic, cationic and non-ionic substantive dyes. The substantive dyes are each used preferably in an amount of 0.001 to 2% by weight, in relation to the weight of the bleaching paste or the alkalizing composition (Alk).

Preferred anionic substantive dyes are the compounds known under the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue. Preferred cationic substantive dyes include cationic triphenylmethane dyes, for example Basic Blue 7, Basic Blue 26, Basic Violet 2 and Basic Violet 14, aromatic systems which are substituted with a quaternary nitrogen group, for example Basic Yellow 57, Basic Red 76, Basic Blue 99, Basic Brown 16 and Basic Brown 17, cationic anthraquinone dyes, such as HC Blue 16 (Bluequat B), as well as substantive dyes including a heterocyclic compound having at least one quaternary nitrogen atom, in particular Basic Yellow 87, Basic Orange 31 and Basic Red 51. The cationic substantive dyes sold under the Arianor trademark are likewise cationic substantive dyes preferred in accordance with the invention. Non-ionic substantive dyes which are suitable are, in particular, nitro and quinone dyes and neutral azo dyes. Preferred non-ionic substantive dyes include the compounds known under the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol. A combination of tetrabromophenol blue and Acid Red 92 is included very particularly preferably in accordance with the invention.

As further optional ingredient, the alkalizing composition used with preference in accordance with the invention includes at least one oxidation dye precursor, which is preferably selected from one or more developer components and optionally one or more coupler components.

At least one oxidation dye precursor is particularly preferably included in a total amount of 0.0001 to 10.0% by weight, preferably 0.001 to 8% by weight, in each case in relation to the weight of the alkalizing composition used with preference in accordance with the invention.

It may be preferred in accordance with the invention to select, as developer component, at least one compound from the group formed from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts thereof.

A developer component is preferably included at least in a total amount of 0.0001 to 10.0% by weight, preferably 0.001 to 8% by weight, in each case in relation to the weight of the alkalizing composition used with preference in accordance with the invention.

Coupler components, within the scope of oxidative dyeing, do not alone form any significant coloration, but instead always require the presence of developer components. It is therefore preferred in accordance with the invention for additionally at least one coupler component to be used when at least one developer component is used.

Coupler components that are preferred in accordance with the invention are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenyl, 5-(2-hydroxyethyl)amino-2-methylphenol, 3-(diethylamino)phenol, N-cyclopentyl-3-aminophenyl, 1,3-dihydroxy-5-(methylamino)benzene, 3-ethylamino-4-methylphenol, 2,4-dichloro-3-aminophenol, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2 hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4-6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or mixtures of these compounds or the physiologically acceptable salts thereof.

At least one coupler component is preferably included in a total amount of 0.0001 to 10.0% by weight, preferably 0.001 to 8% by weight, in each case in relation to the weight of the alkalizing composition used with preference in accordance with the invention.

Here, developer components and coupler components are generally used in approximately equimolar amounts to one another. When the equimolar use has also proven to be expedient, a certain excess of individual oxidation dye precursors is not disadvantageous, and therefore developer components and coupler components can be included in a molar ratio of 1:0.5 to 1:3, in particular 1:1 to 1:2.

The time of action is preferably 5 to 60 min, in particular 5 to 50 min, particularly preferably 10 to 45 min. During the time in which the agent acts on the fibres, it may be advantageous to assist the lightening or color-changing process by adding heat. A phase of action at room temperature likewise corresponds to the invention. In particular, the temperature during the time of action is between 20° C. and 40° C., in particular between 25° C. and 38° C. The agents provide good treatment results even at physiologically acceptable temperatures of less than 45° C. After the end of the color-changing process, all components located on the keratin fibres are rinsed from the hair using water or a surfactant-containing cleansing agent. Here, commercially available shampoo can be used in particular as cleansing agent, wherein it is then possible in particular to dispense with the cleansing agent and to carry out the rinsing process using mains water when the color-changing agent has a higher surfactant content.

A further subject of the present invention is the use of a combination of at least one dicarboxylic acid having 2 to 10 carbon atoms, selected from succinic acid, malic acid, oxalic acid, malonic acid, adipic acid, pimelic acid, suberic acid, azelaic acid, sebacic acid, maleic acid, fumaric acid, D-tartaric acid, L-tartaric acid, meso-tartaric acid, racemic acid, alpha-ketoglutaric acid, beta-ketoglutaric acid, oxaloacetic acid and/or at least one salt of these acids and mixtures of these compounds, wherein the dicarboxylic acid having 2 to 10 carbon atoms is preferably selected from succinic acid, malic acid, maleic acid and the salts of succinic acid, malic acid or maleic acid,
in combination with
at least one amino acid, selected from arginine, lysine, histidine or at least one of the salts of these amino acids,
in a bleaching paste which includes at least one oxidizing agent selected from sodium percarbonates and inorganic salts of a peroxysulfuric acid and mixtures hereof and also 0 to 4% by weight of water, in relation to the weight of the bleaching paste,
for reducing damage to keratinic fibres, in particular human hair, caused by the treatment of these fibres with a mixture of the bleaching paste and an oxidation composition, which, in each case in relation to its weight, includes 50-96% by weight, preferably 70-93% by weight, particularly preferably 80-90% by weight of water and 0.5-20% by weight of hydrogen peroxide and has a pH value in the range of 2.5 to 5.5, measured at 20° C.

That already said with regard to the bleaching pastes according to the invention and the bleaching pastes preferred in accordance with the invention also applies, mutatis mutandis, to the multi-component packaging units (kits-of-parts) according to the invention and those preferred in accordance with the invention.

That already said with regard to the bleaching pastes according to the invention and the bleaching pastes preferred in accordance with the invention also applies, mutatis mutandis, to the methods according to the invention and those preferred in accordance with the invention for lightening and/or changing the color of keratinic fibres.

That already said with regard to the oxidation compositions or alkalizing compositions according to the invention and the oxidation compositions or alkalizing compositions preferred in accordance with the invention also applies, mutatis mutandis, to the multi-component packaging units (kits-of-parts) according to the invention and those preferred in accordance with the invention.

That already said with regard to the oxidation compositions or alkalizing compositions according to the invention and the oxidation compositions or alkalizing compositions preferred in accordance with the invention also applies, mutatis mutandis, to the methods according to the invention and those preferred in accordance with the invention for lightening and/or changing the color of keratinic fibres.

That already said with regard to the bleaching pastes according to the invention and the bleaching pastes preferred in accordance with the invention also applies, mutatis mutandis, to the use according to the invention.

That already said with regard to the oxidation compositions or alkalizing compositions according to the invention and the oxidation compositions or alkalizing compositions preferred in accordance with the invention also applies, mutatis mutandis, to the use according to the invention.

EXAMPLES

1. Bleaching Paste Formulations According to the Invention
(unless specified otherwise, the values correspond to % by weight)

| | No. 1 | No. 2 | No. 3 | No. 4 | No. 5 | No. 6 |
|---|---|---|---|---|---|---|
| Paraffinum Liquidum (Mineral oil) (visc. > 7 mm²/s < 20.5 mm²/s at 20° C.) | 37 | 37 | 37 | 37 | 37 | 37 |
| Ethylene/Propylene/Styrene Copolymer | 0.2 | 0.2 | 0.2 | 0.2 | 0.2 | 0.2 |
| Butylene/Ethylene/Styrene Copolymer | 0.2 | 0.2 | 0.2 | 0.2 | 0.2 | 0.2 |
| Sodium cetearyl sulfate | 0.5 | 0.5 | 0.5 | 0.5 | 0.5 | 0.5 |
| Cetearyl alcohol | 5 | 5 | 5 | 5 | 5 | 5 |
| Ceteareth-50 | 4 | 4 | 4 | 4 | 4 | 4 |
| Castor wax (Hydrogenated Castor Oil) | 0.5 | 0.5 | 0.5 | 0.5 | 0.5 | 0.5 |
| Ceteareth-30 | 0.5 | 0.5 | 0.5 | 0.5 | 0.5 | 0.5 |
| Xanthan Gum | 1.2 | 1.2 | 1.2 | 1.2 | 1.2 | 1.2 |
| Cellulose Gum | 1.2 | 1.2 | 1.2 | 1.2 | 1.2 | 1.2 |
| Sodium metasilicate | 6.5 | 6.5 | 6.5 | 6.5 | 6.5 | 6.5 |
| Potassium persulfate | 41.6 | 41.6 | 41.6 | 41.6 | 41.6 | 41.6 |
| Silica | 0.2 | 0.2 | 0.2 | 0.2 | 0.2 | 0.2 |
| Potassium sulfate | 0.2 | 0.2 | 0.2 | 0.2 | 0.2 | 0.2 |
| Succinic acid | 0.2 | 0.2 | 0.2 | — | — | — |
| Malic acid | — | — | — | 0.2 | 0.2 | 0.2 |
| L-Arginine | 0.2 | 0.4 | — | 0.2 | 0.4 | — |
| L-Lysine | 0.2 | — | 0.4 | 0.2 | — | 0.4 |
| Parfum | 0.6 | 0.6 | 0.6 | 0.6 | 0.6 | 0.6 |

1.2 Developer Emulsion

| Ingredient | Amount (% by weight) |
|---|---|
| Paraffinum Liquidum (Mineral Oil) | 17 |
| Hydrogen peroxide | 6.0 |
| Cetearyl alcohol | 3.5 |
| PEG-40 Castor Oil | 0.7 |
| Sodium cetearyl sulfate | 0.5 |
| Etidronic acid | 0.2 |
| Potassium hydroxide | 0.1 |
| Disodium pyrophosphate | 0.1 |
| Dipicolinic acid (2,6-dicarboxypyridine) | 0.1 |
| Sodium benzoate | 0.1 |
| Water | ad 100 |

The particular bleaching paste and developer emulsion were mixed with one another in a ratio by weight of 1:2.

2. Application 100 g of the freshly produced mixture of the particular bleaching paste and the developer emulsion were applied to dry strands of hair (4 g of mixture per gram of hair).

Once the strands had been bleached for 45 minutes at 32° C., they were washed for 2 minutes using water and dried using a hairdryer.

This bleaching process was repeated once so that the strands were bleached a total of two times in succession.

3. Measurements of the Hair Tensile Strength

Background

Young's modulus is also known as the modulus of elasticity (E-modulus). It corresponds to the ratio of stress to strain with linear elastic behaviour (in Hooke's law).

Hooke's law of elasticity says that the longitudinal change of a body (strain) is linearly dependent on the force causing the deformation (stress).

For moist hair, the linear correlation for strain is from 0 to 2%.

Young's modulus is a measure for the strength of a fibre (the higher the value of Young's modulus, the stronger is the fibre).

The strands used for the measurements consisted of 40 fibres (Kerling International (Backnang, Germany), European Natural Hair 7/0; batch #2014, blend 138).

The mean cross-sectional area of each individual hair was first determined (universal dimensions-measuring device UDM 5000A (Zimmer GmbH, Darmstadt)), more specifically at a temperature of 22° C. and a relative air humidity of 50%. These values are required for the calculation of the stress values.

3.2. Determination of Young's Modulus Prior to the Application of the Bleaching Agent All hair fibres were soaked for one hour in water. They were then stretched (0-1.5% extension) with the stress-strain system MTT 680 with control unit UV 1000 (Dia-Stron Ltd, UK) at a constant speed of 10 mm/min within the elastic phase. The modulus of elasticity (Young's modulus) was then calculated (Software: UvWin 1.32.1000 (Dia-Stron Ltd, UK).

3.3. Determination of Young's Modulus Following the Application of the Bleaching Agent After the four bleaching treatments, the hair fibres were stored for at least 48 hours.

The hair fibres were soaked for one hour in water. They were then stretched (0-1.5% extension) with the stress-strain system MTT 680 with control unit UV 1000 (Dia-Stron Ltd, UK) at a constant speed of 10 mm/min within the elastic phase. The modulus of elasticity (Young's modulus) was then calculated (Software: UvWin 1.32.1000 (Dia-Stron Ltd, UK).

Bleaching treatments lead to a loss of tensile strength of the hair fibres. With the compositions according to the invention however, this tensile strength loss can be reduced to a statistically significant extent.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An anhydrous bleaching paste comprising:
    a) at least one oxidizing agent selected from the group consisting of sodium peroxydisulfate, potassium peroxydisulfate, ammonium peroxydisulfate, and mixtures thereof, wherein the oxidation agent is present in an amount from 2.5 to 65 wt. %,
    b) succinic acid present in the amount of 0.1 to 7 wt. %, converted to mass the mass of free succinic acid,
    c) arginine or a salt arginine, and lysine or a salt of lysine, both present in a combined amount of 0.1 to 7 wt. %, converted to mass of free amino acids, based on the weight of the bleaching paste,
    d) at least one oil in a total amount of 16-60 wt. %.

2. The anhydrous bleaching paste according to claim 1, further comprising at least one inorganic alkalizing agent which is solid at 20° C. and 1013 mbar in a total amount of 0.5-15% by weight.

3. The anhydrous bleaching paste according to claim 1, further comprising at least one substance which thickens the oil, in a total amount of 1-15% by weight.

4. The anhydrous bleaching paste according to claim 1, further comprising at least one substance which thickens the oil selected from the group consisting of copolymers of C2-C4 alkene styrene, linear saturated 1-alkanols having 12-30 carbon atoms, esters of saturated branched or unbranched alkane carboxylic acids having 12 to 24 C atoms, esters of saturated branched or unbranched alcohols having 16 to 50 C atoms, triglycerides of saturated and optionally hydroxylated C12-30 fatty acids, and mixtures of the aforementioned substances,
    wherein the esters have a melting point in the range of 50° C. to 110° C. and wherein the triglycerides have a melting point in the range of 50° C. to 110° C.

5. The anhydrous bleaching paste of claim 1 wherein the oil is in an amount of 25-45% by weight.

6. A method for lightening hair comprising:
    mixing an anhydrous bleaching paste (B) according to claim 1 with an oxidation composition (Ox) which comprises, in each case in relation to its weight, 50-96% by weight hydrogen peroxide and also at least one pH adjustor in such an amount that the oxidation composition has a pH value in the range of 2.5 to 5.5, measured at 20° C., applying the mixture to the hair directly thereafter for 5 to 60 minutes, and
    rinsing the hair with water and optionally using a surfactant-containing cleansing agent,
    wherein the anhydrous bleaching paste (B) and the oxidation composition (Ox) are mixed with one another in a weight-based ratio (B):(Ox) of 0.2-1.

* * * * *